(12) United States Patent
Dow (10) Patent No.: US 12,022,828 B2
(45) Date of Patent: Jul. 2, 2024

(54) WEARABLE DISINFECTING GLOVES

(71) Applicant: ENTJ Enterprises, LLC, Gardner, MA (US)

(72) Inventor: Nicole Dow, Gardner, MA (US)

(73) Assignee: ENTJ Enterprises, LLC, Gardner, MA (US)

( * ) Notice: Subject to any disclaimer, the term of this patent is extended or adjusted under 35 U.S.C. 154(b) by 660 days.

(21) Appl. No.: 17/243,897

(22) Filed: Apr. 29, 2021

(65) Prior Publication Data
US 2022/0346374 A1    Nov. 3, 2022

(51) Int. Cl.
| | |
|---|---|
| *A01N 25/34* | (2006.01) |
| *A01N 33/12* | (2006.01) |
| *A01N 59/00* | (2006.01) |
| *A41D 19/00* | (2006.01) |
| *A47K 7/03* | (2006.01) |
| *A47L 13/19* | (2006.01) |
| *A61L 2/18* | (2006.01) |
| *A61L 2/26* | (2006.01) |
| *B01J 20/24* | (2006.01) |
| *B01J 20/26* | (2006.01) |
| *A61L 101/06* | (2006.01) |
| *A61L 101/08* | (2006.01) |
| *A61L 101/34* | (2006.01) |

(52) U.S. Cl.
CPC ............ *A01N 25/34* (2013.01); *A01N 33/12* (2013.01); *A01N 59/00* (2013.01); *A41D 19/00* (2013.01); *A61L 2/18* (2013.01); *A61L 2/186* (2013.01); *A61L 2/26* (2013.01); *B01J 20/24* (2013.01); *B01J 20/261* (2013.01); *A47K 7/03* (2013.01); *A47L 13/19* (2013.01); *A61L 2101/06* (2020.08); *A61L 2101/08* (2020.08); *A61L 2101/34* (2020.08); *A61L 2202/26* (2013.01)

(58) Field of Classification Search
CPC ........ A01N 25/34; A01N 59/00; A01N 33/12; B01J 20/261; B01J 20/24; A41D 19/00; A61L 2/186; A61L 2/18; A61L 2/26; A61L 2101/06; A61L 2202/26; A61L 2101/08; A61L 2101/34; A46B 5/04; A47K 7/02; A47K 7/03; A47L 13/18; A47L 13/19
USPC ........................................................ 401/6–8
See application file for complete search history.

(56) References Cited

U.S. PATENT DOCUMENTS

| | | | | |
|---|---|---|---|---|
| 3,581,447 A | * | 6/1971 | Falivene | ............... C11D 17/049 |
| | | | | 15/104.93 |
| 3,608,708 A | * | 9/1971 | Storandt | ................. A47L 13/18 |
| | | | | 15/104.94 |
| 3,638,789 A | * | 2/1972 | Tuszewski | ............... A47K 7/02 |
| | | | | 15/104.94 |
| 4,959,881 A | | 10/1990 | Murray | |
| 5,864,883 A | | 2/1999 | Reo | |
| 7,033,100 B2 | | 4/2006 | Barton et al. | |
| (Continued) | | | | |

*Primary Examiner* — David J Walczak
(74) *Attorney, Agent, or Firm* — Intrinsic Law Corp.

(57) ABSTRACT

A wearable disinfecting device includes a skin-protective glove and a disinfecting material. The disinfecting material is attached to the external surface on the palm side of the skin-protective glove. The disinfecting material includes an absorbent material that is at least partially saturated with a disinfecting liquid. The skin-protective glove is chemically resistant to the disinfecting liquid. A protective film that covers the disinfecting material can be releasably attached to the external surface of the skin-protective glove.

10 Claims, 7 Drawing Sheets

(56) References Cited

U.S. PATENT DOCUMENTS

| | | | |
|---|---|---|---|
| D588,769 S | 3/2009 | Nourollah et al. | |
| 8,356,378 B1 * | 1/2013 | Crooms | A47L 13/19 |
| | | | 2/163 |
| D796,762 S | 9/2017 | Rush | |
| 2005/0111898 A1 * | 5/2005 | Barton | A61L 2/26 |
| | | | 401/7 |
| 2008/0216208 A1 | 9/2008 | Sanders | |
| 2014/0096795 A1 | 4/2014 | Farber | |
| 2015/0101138 A1 | 4/2015 | Endee | |

* cited by examiner

WEARABLE DISINFECTING GLOVES

TECHNICAL FIELD

This application relates generally to disinfecting products.

BACKGROUND

There is an increased need, due to the COVID-19 epidemic and the recent attention on viruses and bacteria that may be located on household and publicly shared surfaces for disinfecting products. Example disinfecting products include sprays and liquids. These disinfecting products are typically applied manually by wiping a contaminated surface with a wipe or paper towel.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a wearable disinfecting device comprising: a skin-protective glove having a first external surface and a second external surface, the first external surface configured to be disposed on a palm side of a hand, the second external surface configured to be disposed on a back side of the hand; and a disinfecting material attached to the first external surface of the skin-protective glove, the disinfecting material comprising an absorbent material that is at least partially saturated with a disinfecting liquid, wherein the skin-protective glove is chemically resistant to the disinfecting liquid.

In one or more embodiments, the absorbent material comprises polypropylene, wood pulp, and/or cotton. In one or more embodiments the disinfecting liquid comprises bleach, chlorine, alcohol, hydrogen peroxide, a phenolic compound, a quaternary ammonium compound, or a combination of any of the foregoing.

In one or more embodiments, the device further comprises a protective film disposed on and covering the disinfecting material. In one or more embodiments, the protective film is releasably attached to the first external surface of the skin-protective glove. In one or more embodiments, the protective film includes a tab. The tab can be located on the side of the wrist below the pinky, which can allow for easy removal of the glove after use.

In one or more embodiments, the skin-protective glove includes a palm area, a plurality of fingers and a thumb, and the disinfecting material is attached to the palm area, the plurality of fingers, and/or the thumb of the skin-protective glove. In one or more embodiments, the disinfecting material is attached to the palm area, the fingers, and the thumb of the skin-protective glove. In one or more embodiments, the skin-protective glove comprises polyvinyl chloride, nitrile butadiene rubber, neoprene, polyvinyl alcohol, butyl rubber, and/or latex.

Another aspect of the invention is directed to a wearable disinfecting device comprising: a skin-protective glove having a first external surface and a second external surface, the first external surface configured to be disposed on a palm side of a hand, the second external surface configured to be disposed on a back side of the hand; a first disinfecting layer group attached to the first external surface of the skin-protective glove; and a second disinfecting layer group attached to the first disinfecting layer group. Each of the first and second disinfecting layer groups comprises: an adhesive layer, a disinfecting material attached to the adhesive layer, the disinfecting material comprising an absorbent material that is at least partially saturated with a disinfecting liquid, and a protective film disposed on and covering the disinfecting material. In the first disinfecting layer group, the adhesive layer attaches the disinfecting material to the first external surface of the skin-protective glove. In the second disinfecting layer group, the adhesive layer attaches the disinfecting material to the protective film in the first disinfecting layer group.

In one or more embodiments, the skin-protective glove is chemically resistant to the disinfecting liquid. In one or more embodiments, the disinfecting liquid in the first disinfecting layer group is different than the disinfecting liquid in the second disinfecting layer group. In one or more embodiments, the second disinfecting layer group covers the first disinfecting layer group. In one or more embodiments, the skin-protective glove includes a palm area, a plurality of fingers and a thumb, and the disinfecting material in the first disinfecting layer group is attached to the palm area, the plurality of fingers, and/or the thumb of the skin-protective glove.

In one or more embodiments, the absorbent material comprises polypropylene, wood pulp, and/or cotton. In one or more embodiments, the disinfecting liquid comprises bleach, chlorine, alcohol, hydrogen peroxide, a phenolic compound, a quaternary ammonium compound, or a combination of any of the foregoing. In one or more embodiments, the protective film in the first disinfecting layer group is releasably attached to the first external surface of the skin-protective glove. In one or more embodiments, the protective film in the second disinfecting layer group is attached to the protective film in the first disinfecting layer group. In one or more embodiments, the protective film in the second disinfecting layer group is releasably attached to the first external surface of the skin-protective glove.

Another aspect of the invention is directed to a kit comprising: first and second wearable disinfecting devices, each of the first and second wearable disinfecting devices comprising: a skin-protective glove having a first external surface and a second external surface, the first external surface configured to be disposed on a palm side of a hand, the second external surface configured to be disposed on a back side of the hand; and a disinfecting material attached to the first external surface of the skin-protective glove, the disinfecting material comprising an absorbent material that is at least partially saturated with a disinfecting liquid, wherein the skin-protective glove is chemically resistant to the disinfecting liquid. The kit also comprises a sealed package in which the first and second wearable disinfecting devices are disposed.

BRIEF DESCRIPTION OF THE DRAWINGS

For a fuller understanding of the nature and advantages of the present concepts, reference is made to the detailed description of preferred embodiments and the accompanying drawings.

DETAILED DESCRIPTION

A wearable disinfecting device includes a skin-protective glove and an a disinfecting material attached to the external surface of the skin-protective glove. The disinfecting material is preferably attached to at least the palm side of the skin-protective glove, such as on the external surfaces corresponding to the palm area, the fingers, and the thumb. The disinfecting material includes an absorbent material that can be releasably hold (e.g., through at least partial saturation) a disinfecting liquid. A protective film is disposed on and covers the disinfecting material. An advantage of the protective film is to prevent unintentional contact of the disinfecting material when the user places her hand in the skin-protective glove. The skin-protective glove can be chemically resistant to the disinfecting liquid and can function as a barrier to prevent unintentional contact with a contaminated surface that may include viruses or bacteria.

Figure 1:
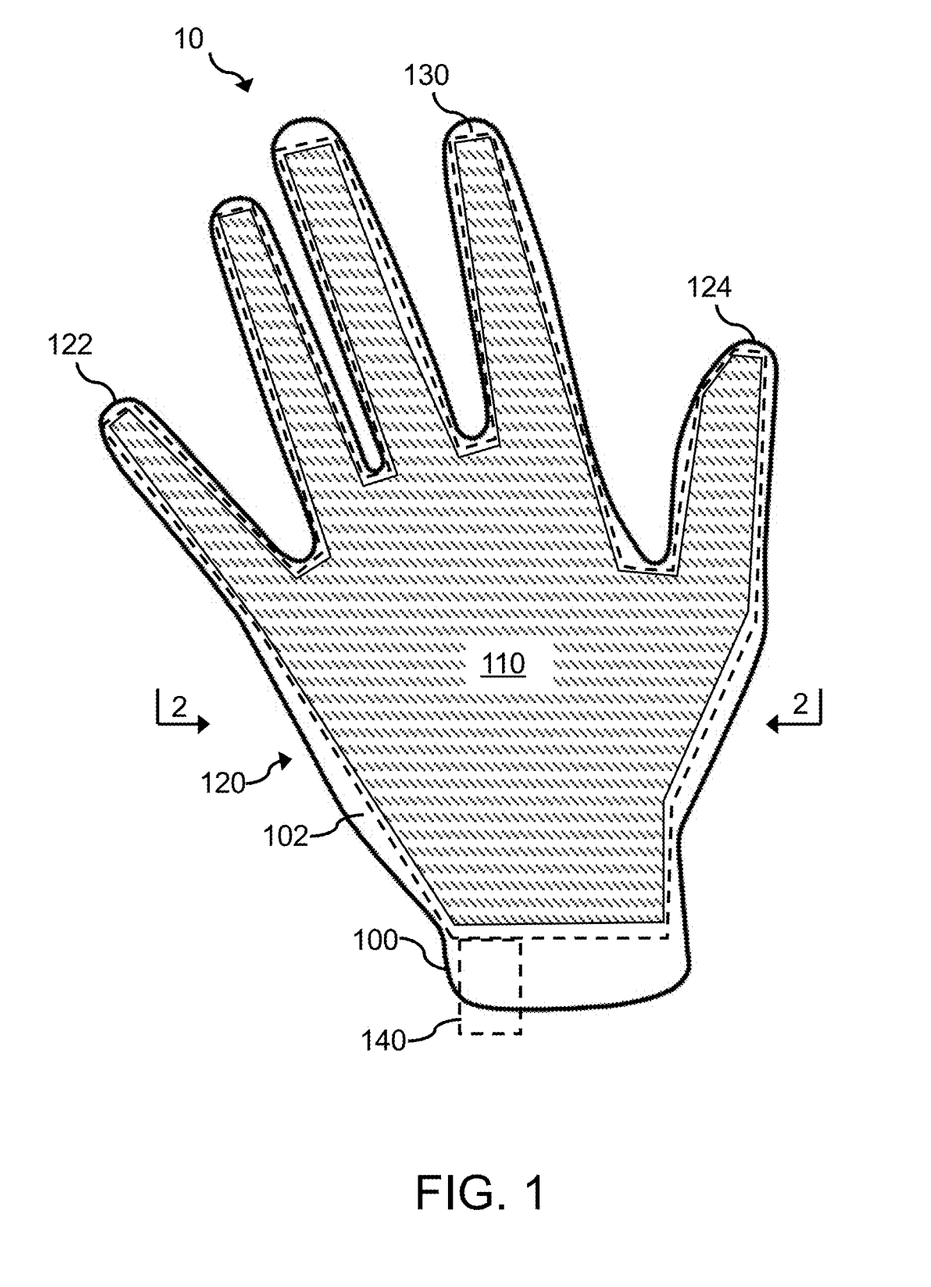
FIG. 1 is a front view of a wearable disinfecting device according to an embodiment.
Figure 2:
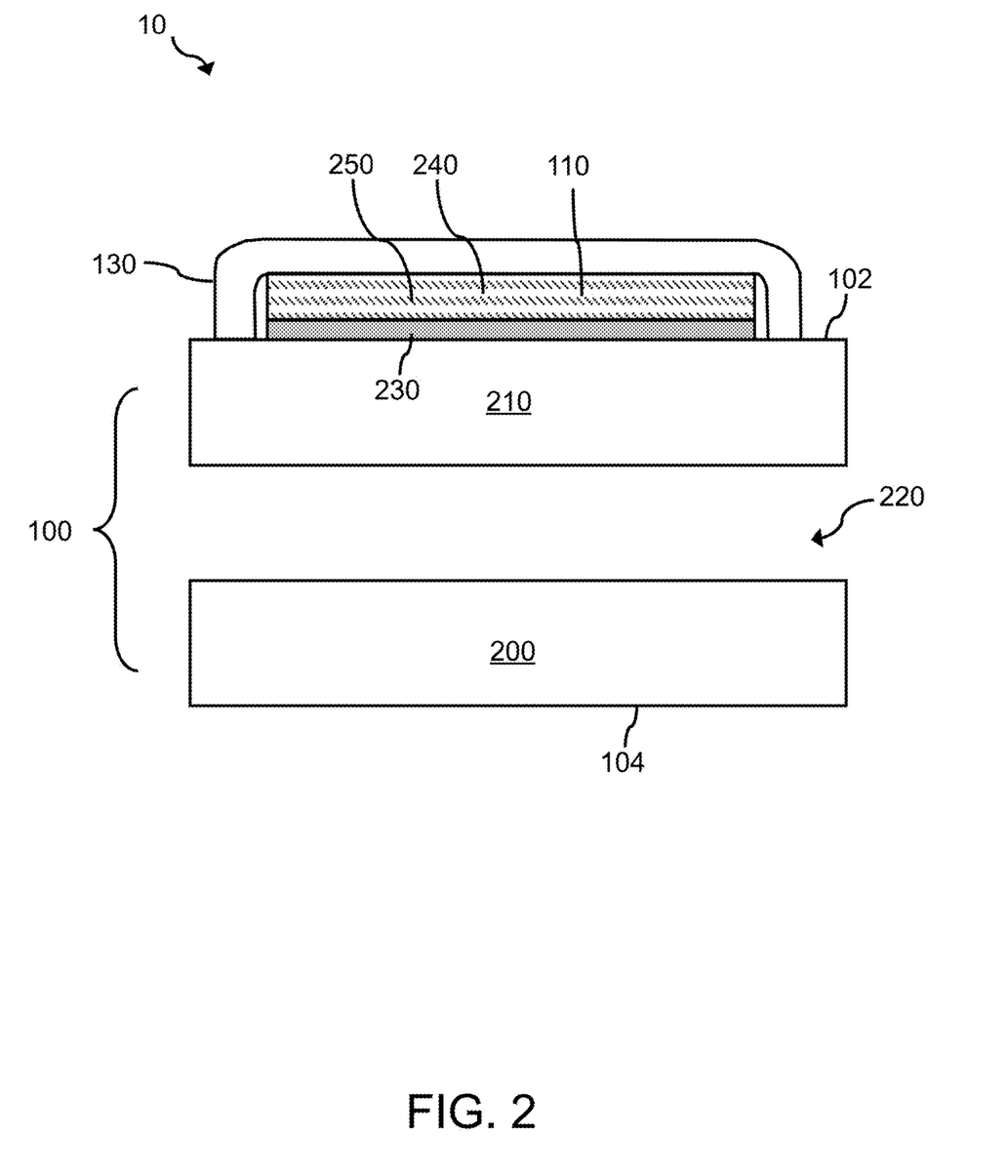
FIG. 2 is a cross-sectional view of the disinfecting device illustrated in FIG. 1 according to an embodiment.

FIG. 1 is a front view of a wearable disinfecting device 10 according to an embodiment. The wearable disinfecting device 10 includes a skin-protective glove 100 and a disinfecting material 110. The disinfecting material 110 is attached to a first external surface 102 (e.g., the external surface on the palm side) of the glove 100. The disinfecting material 110 includes an absorbent material in which a cleaning and/or disinfecting liquid (in general, disinfecting liquid) has been absorbed. For example, the absorbent material can be partially or fully saturated with the disinfecting liquid. The disinfecting material 110 can be attached to some or all of the first external surface 102, including the palm area 120, the fingers 122, and/or the thumb 124 of glove 100. In some embodiments, the disinfecting material 110 is only attached to the first external surface 102 of the glove 100. In other embodiments, the disinfecting material 110 is attached to the first external surface 102, a second external surface 104 (e.g., the back or top side of the hand, as illustrated in FIG. 2) of the glove 100, and/or the region between the first and second external surfaces 102, 104.

The glove 100 can comprise polyvinyl chloride (PVC), nitrile butadiene rubber (NBR), neoprene, polyvinyl alcohol (PVA), butyl rubber, and/or latex. In an example, the glove 100 consists of or comprises a vinyl glove (e.g., a glove formed from PVC). In another example, the glove 100 consists of or comprises a nitrile glove. In another example, the glove 100 consists of or comprises a neoprene glove. In another example, the glove 100 consists of or comprises a PVA glove. In another example, the glove 100 consists of or comprises a butyl rubber glove. In another example, the glove 100 consists of or comprises a latex glove. In another example, the glove 100 consists of or comprises a latex/nitrile blended glove. In another example, the glove 100 consists of or comprises a vinyl/nitrile blended glove. The glove 100 is preferably disposable.

A protective film 130 can be disposed on and can cover the disinfecting material 110. The protective film 130 can consist of or can comprise low-density polyethylene, polyvinyl alcohol, and/or another material. The protective film 130 can be partially or fully optically transparent in some embodiments. Alternatively, the protective film 130 can be opaque. The protective film 130 is preferably flexible. The protective film 130 can have dimensions that are slightly larger than the corresponding dimensions of disinfecting material 110. For example, the protective film 130 can have dimensions that are about 1 mm to about 3 mm larger than the corresponding dimensions of disinfecting material 110. In some embodiments, the protective film 130 can have dimensions that are the same or about the same as the corresponding dimensions of the first external surface 102 of the glove 100. As used herein, "about" means plus or minus 10% of the relevant value.

The protective film 130 can adhere to the first external surface 102 of the glove 100 such as by electrostatic clinging or through an adhesive. Additionally or alternatively, the protective film 130 can adhere to the disinfecting material 110. The protective film 130 can be released by pulling the protective film 130 away from the disinfecting material 110 and glove 100. In some embodiments, the protective film 130 can be released by pulling on a tab 140 can be attached to the protective film 130. The tab 140 can comprise the same material or a different material than the protective film 130. The tab 140 can be located near the wrist (e.g., below the pinky) of the subject when the glove 100 is worn by the subject. Another tab can allow for easy removal of the glove 100 after use. Alternatively, the tab 140 can be located in another position with respect to the subject. The protective film 130 can prevent or reduce the evaporation of the disinfecting liquid during transport and storage of the disinfecting device 10. In addition, the protective film 130 can function as a protective barrier for safe handling of the disinfecting device 10.

FIG. 2 is a cross-sectional view of disinfecting device 10 through plane 2-2 in FIG. 1 according to an embodiment. As illustrated, the glove 100 includes a bottom barrier layer 200 and a top barrier layer 210 that define a hollow region 220 to insert a hand. An adhesive layer 230 is disposed on the first external surface 102 of the glove 100 (e.g., on the top layer 210). The adhesive layer 230 can comprise a rubber-based adhesive such as contact cement, epoxy, and/or cyanoacrylate (e.g., Super Glue). The adhesive can have high-performance bonding. The disinfecting material 110 is disposed on the adhesive layer 230. The protective film 130 is disposed on the disinfecting material 110. The bottom and top barrier layers 200, 210 can function as protective barriers to prevent or limit contact between the hand and the disinfecting material 110, which can be harmful and/or irritating to unprotected skin. In addition, the bottom and top barrier layers 200, 210 can protect the skin from contacting bacteria, viruses, and/or other substances that may be on a surface to be disinfected using disinfecting device 10.

The disinfecting material 110 includes an absorbent material 240 in which a disinfecting liquid 250 has been absorbed. For example, the absorbent material 240 can be pre-soaked (e.g., partially or fully saturated) with the disinfecting liquid 250. The absorbent material 240 can comprise polypropylene, wood pulp, cotton, or a combination of two or more of the foregoing. Polypropylene can provide or improve durability of the absorbent material 240. Alternatively, the absorbent material 240 can comprise another absorbent material. The absorbent material 240 is configured to releasably retain a volume or mass of the disinfecting liquid 250. The disinfecting liquid can comprise bleach (e.g., a sodium hypochlorite solution), chlorine, alcohol (e.g., ethanol, isopropyl alcohol), hydrogen peroxide, a phenolic compound, a quaternary ammonium compound (e.g., benzalkonium chloride, quaternary ammonia), an alkyl (e.g., a mixture of 50% $C_{14}$, 40% $C_{12}$, and 10% $C_{16}$), dimethyl benzyl ammonium chlorides, dimethyl benzyl ammonium saccharinate, ethanol, cutaneous solution chloroxylenol, and/or another chemical disinfectant such as a household disinfectant or an industrial disinfectant. The material of the glove 100, including the bottom and top barrier layers 200, 210, is preferably chemically resistant (e.g., at least partially chemically resistant) to the disinfecting liquid 250.

In use, the user opens a sealed package that includes a pair of gloves 100. As the user puts his or her hand in each glove 100, the protective film 130 prevents the user's unprotected skin from touching the disinfecting material 110, which can be harmful and/or irritating. After the gloves 100 are on the user's hands, the user can remove the protective film 130 (e.g., using tab 140) to expose the disinfecting material 110. The user can then clean or disinfect a surface by wiping the surface with the disinfecting material 110. After the disinfecting liquid 250 is used up and/or the disinfecting material 110 is dirty, the user can remove and dispose of the gloves 100.

Figure 3:
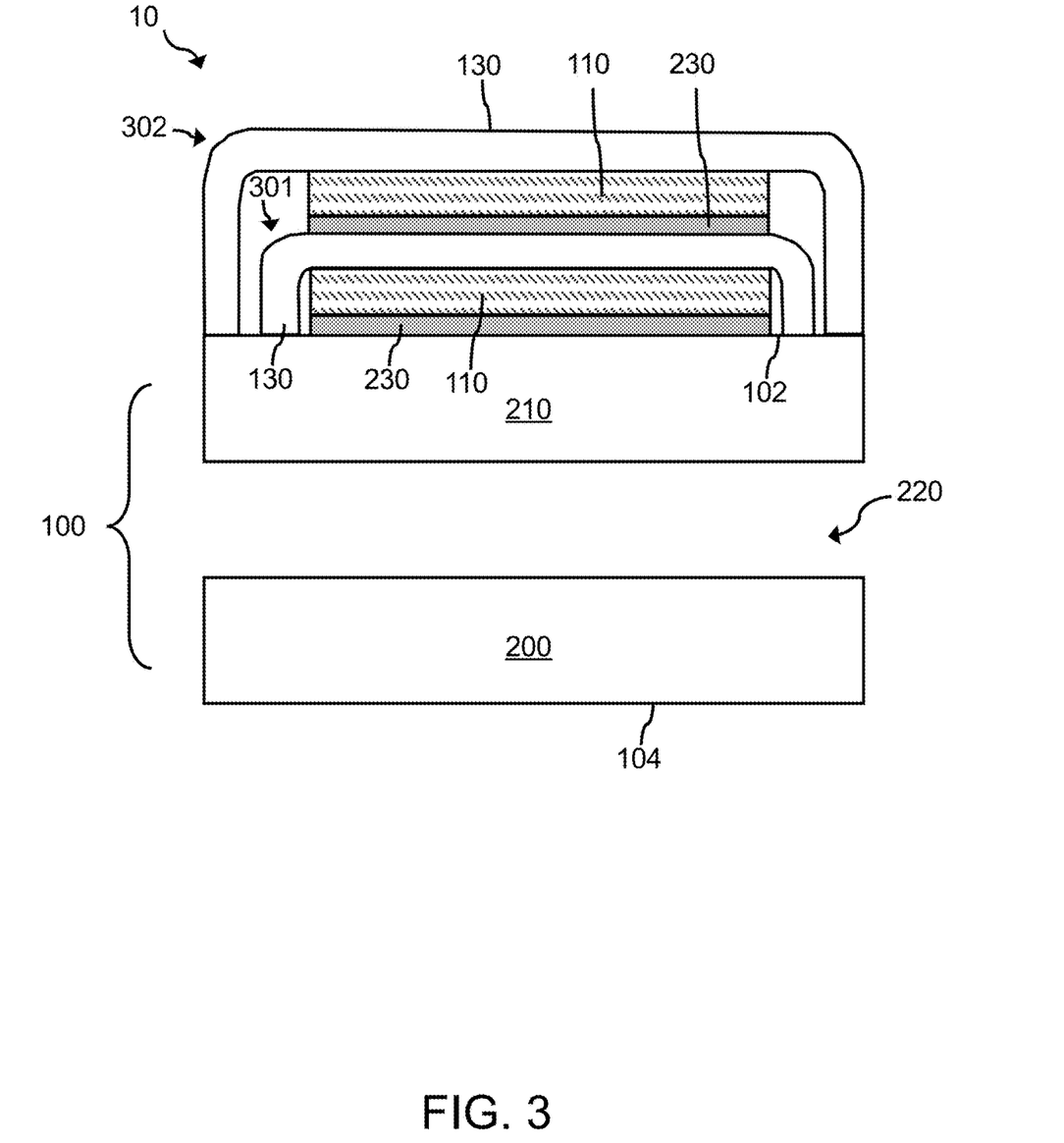
FIG. 3 is a cross-sectional view of the disinfecting device illustrated in FIG. 1 according to an alternative embodiment.

FIG. 3 is a cross-sectional view of disinfecting device 10 through plane 2-2 in FIG. 1 according to an alternative embodiment. The cross-sectional view illustrated in FIG. 3 is the same as that in FIG. 2 except that in FIG. 3 there are a plurality of layers of adhesive 230, disinfecting material 110, and protective film 130. For example, the disinfecting device 10 can include a first disinfecting layer group 301 and a second disinfecting layer group 302. The first disinfecting layer group 301 is disposed on the top layer 210 of the glove 100 (e.g., on the first external surface 102). The second disinfecting layer group 302 is disposed on the first disinfecting layer group 301. The second disinfecting layer group 302 can cover the first disinfecting layer group 301. For example, the dimensions and/or locations of the second disinfecting layer group 302 with respect to the first external surface 102 can be the same or about the same as the dimensions and/or locations of the first disinfecting layer group 301 with respect to the first external surface 102.

Each disinfecting layer group 301, 302 includes adhesive layer 230, disinfecting material 110, and protective film 130. The disinfecting device 10 can include additional disinfecting layer groups, such as a third disinfecting layer group or additional disinfecting layer groups. The disinfecting material 110 in each disinfecting layer group can include the same disinfecting liquid 250 or a different disinfecting liquid 250.

Figure 6:
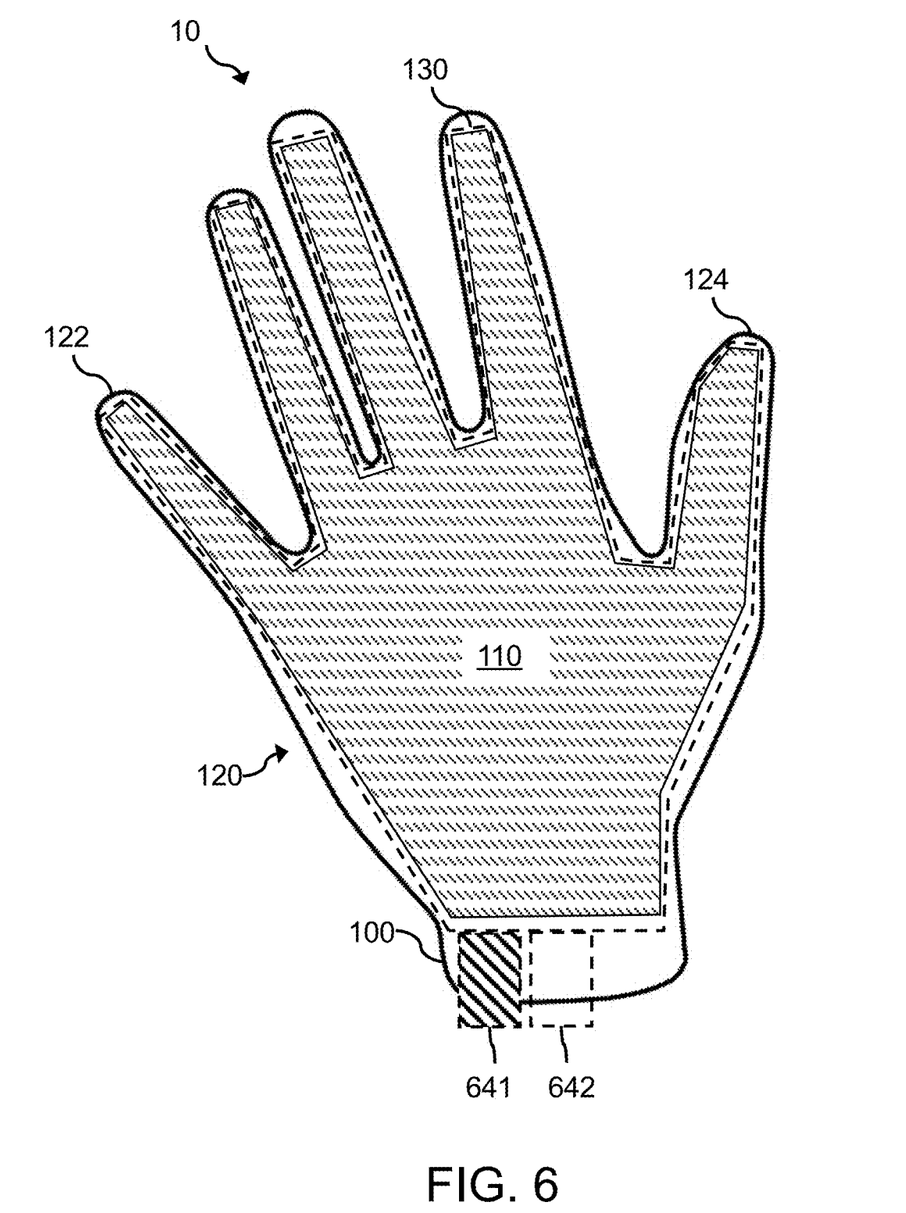
FIG. 6 is a front view of a wearable disinfecting device according to an embodiment.

The adhesive layer 230 in the second disinfecting layer group 302 is disposed on the protective film 130 in the first disinfecting layer group 301. Thus, the adhesive layer 230 in the second disinfecting layer group 302 can attach the second disinfecting layer group 302 to the first disinfecting layer group 301. Each protective film 130 is releasably attached to the first external surface 102 of the glove 100 such as by electrostatic clinging. Each protective film 130 can have a corresponding tab 641, 642, as illustrated in FIG. 6. Tab 641 can be attached to the protective film 130 in the first disinfecting layer group 301. Tab 642 can be attached to the protective film 130 in the second disinfecting layer group 302. The tabs 641, 642 can be located near the wrist (e.g., below the pinky) of the subject when the glove 100 is worn by the subject. The tabs 641, 642 can be disposed next to each other, on top of each other, overlapping each other, or in other relative locations from each other. An additional tab can be located near the wrist (e.g., below the pinky) of the subject when the glove 100 is worn by the subject to allow for easy removal of the glove 100 after use.

Figure 4:
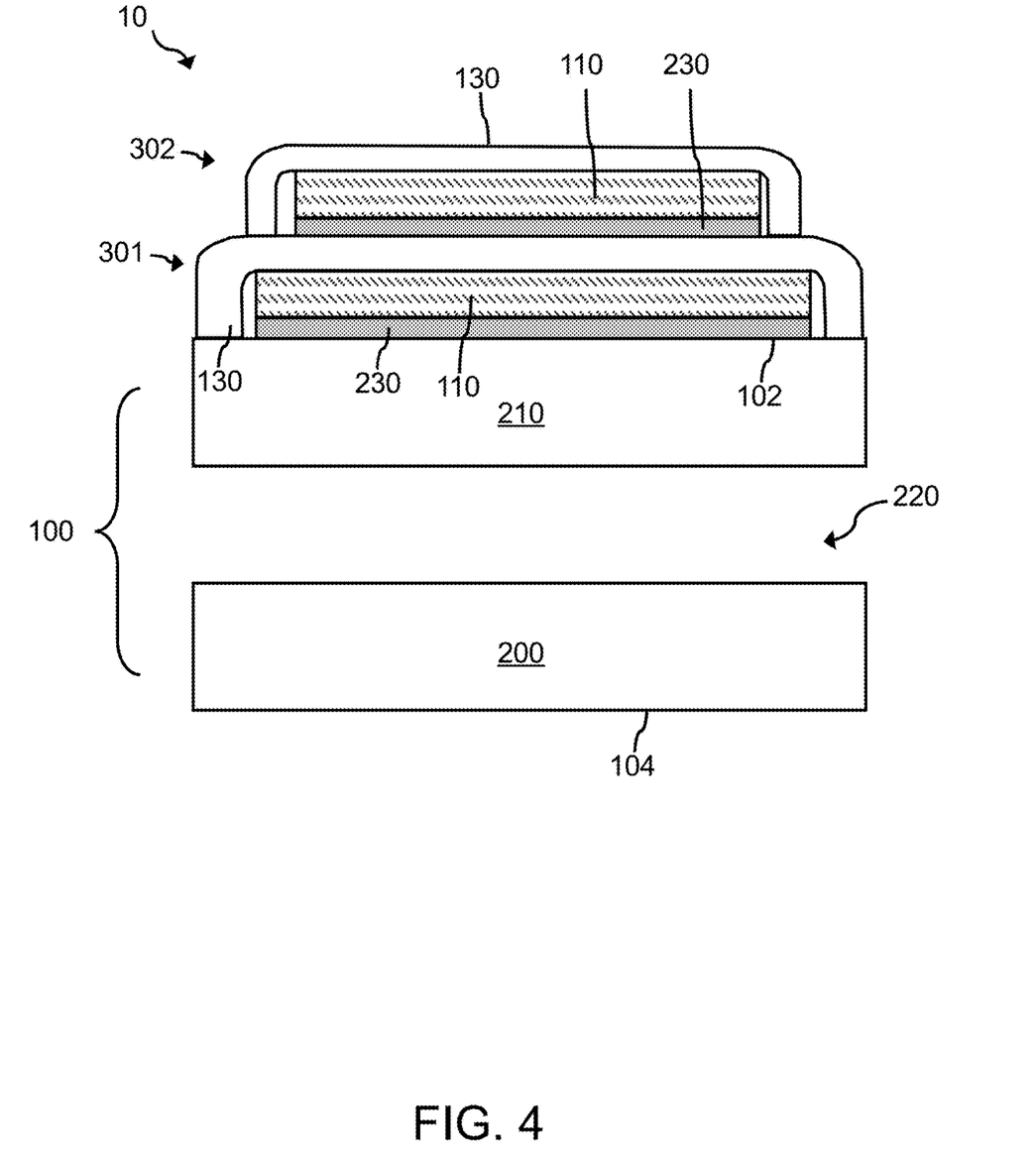
FIG. 4 is a cross-sectional view of the disinfecting device illustrated in FIG. 1 according to another alternative embodiment.

FIG. 4 is a cross-sectional view of disinfecting device 10 through plane 2-2 in FIG. 1 according to another alternative embodiment. The cross-sectional view illustrated in FIG. 4 is the same as that in FIG. 3 except that in FIG. 4 the protective film 130 in the second disinfecting layer group 302 is releasably attached (e.g., such as by electrostatic clinging) to the protective film 130 in the first disinfecting layer group 301.

Figure 5:
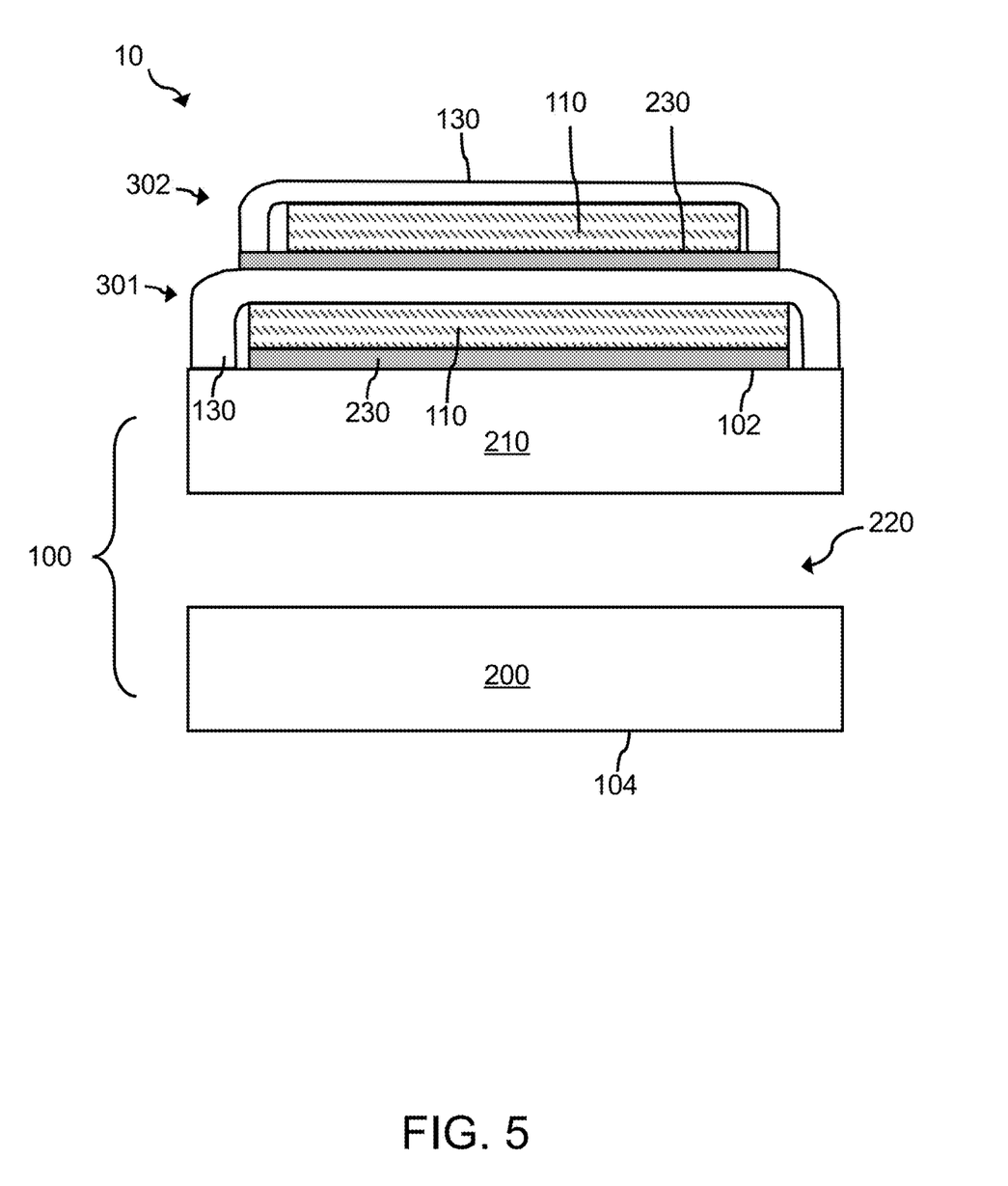
FIG. 5 is a cross-sectional view of the disinfecting device illustrated in FIG. 1 according to another alternative embodiment.

FIG. 5 is a cross-sectional view of disinfecting device 10 through plane 2-2 in FIG. 1 according to another alternative embodiment. The cross-sectional view illustrated in FIG. 5 is the same as that in FIG. 4 except that in FIG. 4 the protective film 130 in the second disinfecting layer group 302 is attached to the protective film 130 in the first disinfecting layer group 301 using the adhesive layer 230 in the second disinfecting layer group 302.

In use, the user opens a sealed package that includes a pair of gloves 100. As the user puts her hand in each glove 100, the protective film 130 in the second disinfecting layer group 302 prevents the user's unprotected skin from touching the disinfecting material 110 in the second disinfecting layer group 302, which can be harmful and/or irritating. After the gloves 100 are on the user's hands, the user can remove the protective film 130 in the second disinfecting layer group 302 (e.g., using tab 642) to expose the disinfecting material 110 in the second disinfecting layer group 302. The user can then clean or disinfect a surface by wiping the surface with the disinfecting material 110 in the second disinfecting layer group 302. After the disinfecting liquid 250 is used up and/or the disinfecting material 110 is dirty, the user removes the protective film 130 in the first disinfecting layer group 301 (e.g., using tab 641) to expose the disinfecting material 110 in the first disinfecting layer group 301. The user can then clean or disinfect a surface by wiping the surface with the disinfecting material 110 in the first disinfecting layer group 301. After the disinfecting liquid 250 is used up and/or the disinfecting material 110 is dirty, the user can remove and dispose of the gloves 100.

Figure 7:
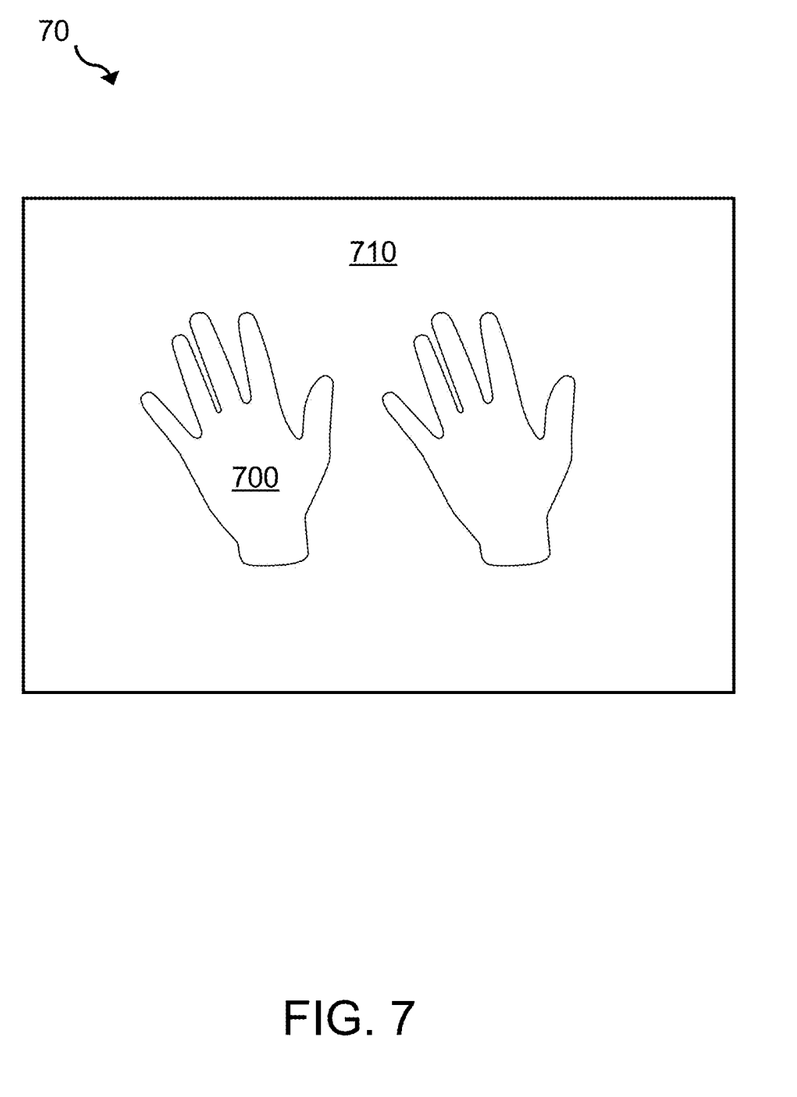
FIG. 7 is a block diagram of a kit according to an embodiment.

FIG. 7 is a block diagram of a kit 70 according to an embodiment. The kit 70 includes a pair of wearable disinfecting devices 700 that are disposed in a sealed package 710. Each wearable disinfecting device 700 can be the same as wearable disinfecting device 10. One of the wearable disinfecting devices 700 can be configured to fit and receive the left hand of a user. The other wearable disinfecting device 700 can be configured to fit and receive the right hand of the user.

The invention should not be considered limited to the particular embodiments described above, but rather should be understood to cover all aspects of the invention as fairly set out in the attached claims. Various modifications, equivalent processes, as well as numerous structures to which the invention may be applicable, will be apparent to those skilled in the art to which the invention is directed upon review of this disclosure. The claims are intended to cover such modifications and equivalents.

What is claimed is:

1. A wearable disinfecting device comprising:
a skin-protective glove having a first external surface and a second external surface, the first external surface configured to be disposed on a palm side of a hand, the second external surface configured to be disposed on a back side of the hand;
a first disinfecting layer group attached to the first external surface of the skin-protective glove; and
a second disinfecting layer group attached to the first disinfecting layer group,
wherein:
each of the first and second disinfecting layer groups comprises:
an adhesive layer,
a disinfecting material attached to the adhesive layer, the disinfecting material comprising an absorbent material that is at least partially saturated with a disinfecting liquid, and
a protective film disposed on and covering the disinfecting material,
in the first disinfecting layer group, the adhesive layer attaches the disinfecting material to the first external surface of the skin-protective glove, and
in the second disinfecting layer group, the adhesive layer attaches the disinfecting material to the protective film in the first disinfecting layer group.

2. The disinfecting device of claim 1, wherein the skin-protective glove is chemically resistant to the disinfecting liquid.

3. The disinfecting device of claim 1, wherein the disinfecting liquid in the first disinfecting layer group is different than the disinfecting liquid in the second disinfecting layer group.

4. The disinfecting device of claim 1, wherein the second disinfecting layer group covers the first disinfecting layer group.

5. The disinfecting device of claim 4, wherein:
the skin-protective glove includes a palm area, a plurality of fingers and a thumb, and
the disinfecting material in the first disinfecting layer group is attached to the palm area, the plurality of fingers, and/or the thumb of the skin-protective glove.

6. The disinfecting device of claim 1, wherein the absorbent material comprises polypropylene, wood pulp, and/or cotton.

7. The disinfecting device of claim 1, wherein the disinfecting liquid comprises bleach, chlorine, alcohol, hydrogen peroxide, a phenolic compound, a quaternary ammonium compound, or a combination of any of the foregoing.

8. The disinfecting device of claim 1, wherein the protective film in the first disinfecting layer group is releasably attached to the first external surface of the skin-protective glove.

9. The disinfecting device of claim 8, wherein the protective film in the second disinfecting layer group is attached to the protective film in the first disinfecting layer group.

10. The disinfecting device of claim 8, wherein the protective film in the second disinfecting layer group is releasably attached to the first external surface of the skin-protective glove.

* * * * *